United States Patent [19]
Køhnke

[11] Patent Number: 5,797,863
[45] Date of Patent: Aug. 25, 1998

[54] COLLAPSIBLE CERVICAL COLLAR

[75] Inventor: Ole Køhnke, Frederiksberg, Denmark

[73] Assignee: Ambu International A/S, Glostrup, Denmark

[21] Appl. No.: 758,562

[22] Filed: Nov. 29, 1996

[51] Int. Cl.[6] .................................................. A61F 5/00
[52] U.S. Cl. ................................. 602/18; 128/DIG. 23
[58] Field of Search ........................... 602/5, 17, 18; 128/DIG. 23

[56] References Cited

U.S. PATENT DOCUMENTS

| | | |
|---|---|---|
| Re. 32,219 | 8/1986 | Garth . |
| Re. 34,714 | 8/1994 | Burns ........................... 602/18 |
| 591,338 | 10/1897 | Fortney et al. ............ 128/DIG. 23 X |
| 2,102,069 | 12/1937 | Hanicke . |
| 2,223,276 | 11/1940 | Ward . |
| 2,692,595 | 10/1954 | Blair, Jr. . |
| 2,735,424 | 2/1956 | Benjamin . |

(List continued on next page.)

FOREIGN PATENT DOCUMENTS

| | | |
|---|---|---|
| 2 507 887 | 12/1982 | France . |
| 918770 | 2/1955 | Germany . |
| 1199921 | 9/1965 | Germany . |
| 2129140 | 12/1972 | Germany . |
| 2404683 C3 | 8/1975 | Germany . |
| 3308571 A1 | 9/1984 | Germany . |
| 3318938 A1 | 11/1984 | Germany . |
| 3929347 A1 | 3/1990 | Germany . |
| 3905115 A1 | 8/1990 | Germany . |
| 3906233 A1 | 8/1990 | Germany . |
| 1132607 | 11/1968 | United Kingdom . |
| 2049436 | 12/1980 | United Kingdom . |
| 2165157 | 4/1986 | United Kingdom . |
| 2165762 | 4/1986 | United Kingdom . |
| 2182851 | 5/1987 | United Kingdom . |
| 2233900 | 1/1991 | United Kingdom . |
| 2234905 | 2/1991 | United Kingdom . |

*Primary Examiner*—Richard J. Apley
*Assistant Examiner*—Denise Pothier
*Attorney, Agent, or Firm*—Cammarata & Grandinetti

[57] ABSTRACT

A collapsible cervical collar is disclosed with an elongated neck encircling band and a chin support brace. The chin support brace has first and second ends and a concave edge separating the first and second ends. A hinge connects the elongated neck encircling band to the chin support brace. The hinge enables the chin support brace to rotate more than 180 degrees relative to the elongated neck encircling band from an inoperable or flat condition to an operable three-dimensional condition.

9 Claims, 10 Drawing Sheets

U.S. PATENT DOCUMENTS

| | | | |
|---|---|---|---|
| 2,736,314 | 2/1956 | Hale . | |
| 2,801,630 | 8/1957 | Moore . | |
| 2,806,471 | 9/1957 | Breese . | |
| 2,807,260 | 9/1957 | Teufel . | |
| 2,818,063 | 12/1957 | Smith et al. . | |
| 2,820,455 | 1/1958 | Hall . | |
| 2,828,736 | 4/1958 | Monfardini . | |
| 2,904,040 | 9/1959 | Hale . | |
| 2,911,970 | 11/1959 | Bartels . | |
| 3,024,784 | 3/1962 | Monfardini . | |
| 3,027,894 | 4/1962 | Moore . | |
| 3,042,026 | 7/1962 | Monfardini . | |
| 3,042,027 | 7/1962 | Monfardini . | |
| 3,050,052 | 8/1962 | Grassl . | |
| 3,055,358 | 9/1962 | Di Palma et al. . | |
| 3,070,090 | 12/1962 | Taylor . | |
| 3,075,521 | 1/1963 | Grassl . | |
| 3,135,256 | 6/1964 | Gruber . | |
| 3,164,151 | 1/1965 | Nicoll . | |
| 3,220,406 | 11/1965 | Connelly . | |
| 3,285,243 | 11/1966 | Yellin . | |
| 3,285,244 | 11/1966 | Cottrell . | |
| 3,295,516 | 1/1967 | Grassl . | |
| 3,306,284 | 2/1967 | McKinley . | |
| 3,313,297 | 4/1967 | Applegate et al. . | |
| 3,320,950 | 5/1967 | McElvenny . | |
| 3,343,532 | 9/1967 | Zumaglini . | |
| 3,364,926 | 1/1968 | Alderson . | |
| 3,374,785 | 3/1968 | Gaylord, Jr. . | |
| 3,397,688 | 8/1968 | Gottfried . | |
| 3,504,667 | 4/1970 | McFarlane . | |
| 3,507,273 | 4/1970 | Yellin . | |
| 3,512,523 | 5/1970 | Barnett . | |
| 3,530,853 | 9/1970 | Bond . | |
| 3,572,328 | 3/1971 | Bond . | |
| 3,696,810 | 10/1972 | Gaylord, Jr. . | |
| 3,724,452 | 4/1973 | Nitschke . | |
| 3,756,226 | 9/1973 | Calabrese et al. . | |
| 3,850,164 | 11/1974 | Hare . | |
| 3,905,362 | 9/1975 | Eyrick et al. . | |
| 3,916,884 | 11/1975 | Attenburrow . | |
| 3,916,885 | 11/1975 | Gaylord, Jr. . | |
| 3,921,626 | 11/1975 | Neel . | |
| 3,964,474 | 6/1976 | Fox . | |
| 4,041,940 | 8/1977 | Frankel et al. . | |
| 4,043,325 | 8/1977 | Ochs et al. . | |
| 4,141,368 | 2/1979 | Meyer . | |
| 4,151,842 | 5/1979 | Miller . | |
| 4,194,501 | 3/1980 | Watt . | |
| 4,204,529 | 5/1980 | Cochrane . | |
| 4,205,667 | 6/1980 | Gaylord, Jr. . | |
| 4,232,663 | 11/1980 | Newton . | |
| 4,299,209 | 11/1981 | Behrens et al. . | |
| 4,325,363 | 4/1982 | Berkeley . | |
| 4,383,523 | 5/1983 | Schurman . | |
| 4,401,111 | 8/1983 | Blackstone . | |
| 4,413,619 | 11/1983 | Grath . | |
| 4,515,153 | 5/1985 | Calabrese . | |
| 4,520,801 | 6/1985 | Lerman . | |
| 4,538,597 | 9/1985 | Lerman . | |
| 4,543,947 | 10/1985 | Blackstone . | |
| 4,562,833 | 1/1986 | Pujals, Jr. . | |
| 4,582,051 | 4/1986 | Greene et al. . | |
| 4,589,407 | 5/1986 | Koledin et al. . | |
| 4,628,913 | 12/1986 | Lerman . | |
| 4,643,174 | 2/1987 | Horiuchi . | |
| 4,643,719 | 2/1987 | Garth et al. . | |
| 4,702,233 | 10/1987 | Omicioli . | |
| 4,708,129 | 11/1987 | Pujals, Jr. . | |
| 4,712,540 | 12/1987 | Tucker et al. | 602/18 |
| 4,782,824 | 11/1988 | Davies | 602/18 |
| 4,793,334 | 12/1988 | McGuiness | 602/18 |
| 4,794,917 | 1/1989 | O'Leary . | |
| 4,819,622 | 4/1989 | Taylor et al. . | |
| 4,827,915 | 5/1989 | Gorsen . | |
| 4,886,052 | 12/1989 | Calabrese . | |
| 4,940,043 | 7/1990 | Burn et al. | 602/18 |
| 4,955,368 | 9/1990 | Heimann . | |
| 4,969,453 | 11/1990 | Heimann . | |
| 4,987,891 | 1/1991 | Gaylord, Jr. et al. . | |
| 5,003,968 | 4/1991 | Mars . | |
| 5,005,563 | 4/1991 | Veale . | |
| 5,005,564 | 4/1991 | Grundei et al. . | |
| 5,010,877 | 4/1991 | Druskoczi . | |
| 5,029,577 | 7/1991 | Sarkozi . | |
| 5,038,759 | 8/1991 | Morgenstern . | |
| 5,048,509 | 9/1991 | Grundei et al. . | |
| 5,054,475 | 10/1991 | Calabrese et al. . | |
| 5,058,572 | 10/1991 | Schmid et al. . | |
| 5,060,637 | 10/1991 | Schmid et al. . | |
| 5,083,553 | 1/1992 | Stevenson . | |
| 5,088,482 | 2/1992 | McGuinness | 128/DIG. 23 X |
| 5,097,824 | 3/1992 | Garth . | |
| 5,163,941 | 11/1992 | Garth et al. . | |
| 5,171,296 | 12/1992 | Herman . | |
| 5,180,361 | 1/1993 | Moore et al. . | |
| 5,211,185 | 5/1993 | Garth et al. . | |
| 5,215,517 | 6/1993 | Stevenson et al. | 602/18 |
| 5,230,698 | 7/1993 | Garth . | |
| 5,366,438 | 11/1994 | Martin, Sr. . | |
| 5,409,450 | 4/1995 | Donelson | 602/17 X |
| 5,520,619 | 5/1996 | Martin . | |
| 5,588,957 | 12/1996 | Martin, Sr. . | |
| 5,624,387 | 4/1997 | McGuinness | 602/18 |

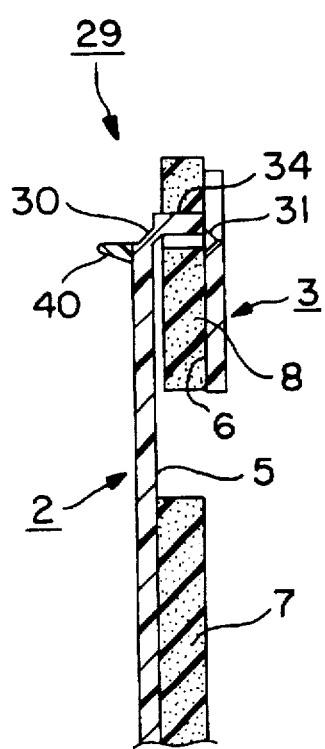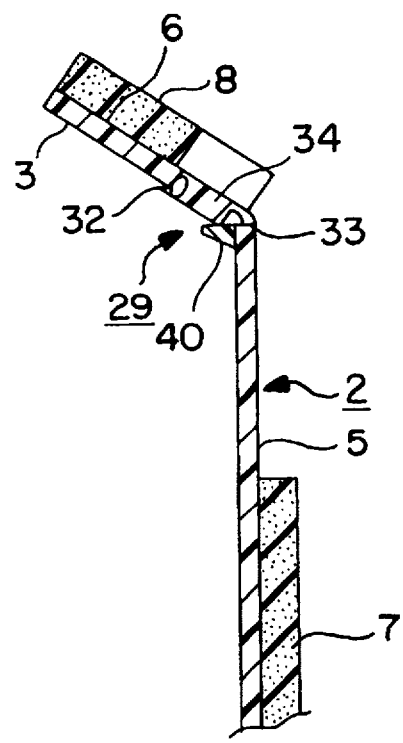

COLLAPSIBLE CERVICAL COLLAR

This application claims the benefit of U.S. Provisional Application Number 60/007,822 filed on Nov. 30, 1995.

BACKGROUND OF THE INVENTION

1. Field of the Invention

This invention relates to cervical collars. This invention is specifically concerned with a cervical collar that collapses into a substantially flattened, inoperable configuration.

2. Description of the Background Art

The use of cervical collars to restrict the movement of the head and neck of a patient, who has suffered a neck or spinal injury, is well known in the art. In fact, cervical collars are now standard equipment for emergency medical service squads and rescue units.

Early cervical collars had disadvantages that prohibit their current use. For example, early cervical collars did not provide access to a patient's neck to enable the performance of a tracheotomy or other procedure. Current and anticipated regulations prohibit the reuse of virtually all medical products exposed to body fluids. The expense of complex cervical collars is a significant factor, in view of these regulations, that prevents the use of complex cervical collars as disposable items.

Some cervical collars collapse into a substantially flattened configuration without complete disassembly of their parts. A substantial amount of storage space is, therefore, saved transporting and storing such cervical collars on emergency vehicles and at hospitals.

Cervical collars are, typically, constructed from relatively stiff, light-weight synthetic resins. Many synthetic resins or plastics are capable of bending from a flat condition into a cylindrical condition to encircle the neck and provide substantial support for the wearer.

U.S. Pat. No. 3,027,894 to Moore discloses a cervical collar constructed from relatively heavy strap-like materials, such as leather. Such bulky cervical collars often include multiple metal braces to immobilize the head of a patient. These cervical collar of this patent, however, is cumbersome to use and expensive to produce.

U.S. Reissue Pat. No. Re. 32,219 to Garth discloses a cervical collar having a rotatable, one-piece chin support brace manufactured from synthetic resin. This one-piece chin support brace comprises a relatively rigid, C-shaped, plastic member joined to the body of the cervical collar at two fixed points. One of the fixed points is in the center of the chin support brace, and the other point is at one end of the chin support brace. In operation, the end of the chin support brace, which is not permanently affixed to the body of the collar, is rotated upward. This rotation bends the chin support brace outward. After this outward bending is complete, the end of the chin support brace is secured to the body of the cervical collar by a rivet or snap fastener. The cervical collar cannot be manipulated into a completely flattened configuration.

U.S. Pat. No. 3,164,151 to Nicoll discloses an inflatable splint. The inflatable splint is used as a cervical collar. Minimal space is required to store the collar when it is deflated. However, puncturing the collar renders it inoperable. The collar cannot be safely used unless it is properly inflated.

U.S. Pat. No. 4,712,540 to Tucker et al. discloses a cervical collar. The cervical collar comprises a flexible panel and a chin support member extending therefrom. The chin support member is located against the outer surface of the panel when the panel is flat. A flexible ribbon at each end of the member and a central projecting tab uncoil to project the chin support member over the panel when the panel is formed into a neck encircling band. Returning the panel to a flattened orientation twists the ribbons and tab and swivels the chin support member back to a position against the outer surface of the panel. Successive twisting and uncoiling of the ribbons and tab eventually weaken these thin projections of synthetic resin. The ribbons and tab, therefore, gradually lose their ability to flip or rotate the member over the panel and to adequately support the chin.

The industry lacks a sturdy inexpensive cervical collar that can be stored in a flat condition and bent without further assembly into an operable condition and that retains its rigidity throughout numerous uses.

SUMMARY OF THE INVENTION

The collapsible cervical collar has an elongated neck encircling band and a chin support brace. The chin support brace has first and second ends and a concave edge separating the first and second ends. A hinge means connects the elongated neck encircling band to the chin support brace. The hinge means enables the chin support brace to rotate more than 180 degrees from an inoperable position, that is coplanar with the elongated neck encircling band, to an operable position. The collapsible cervical collar is collapsible from an operable configuration to a flattened configuration. Specifically, the present invention relates to a collapsible cervical collar comprising:

an elongated neck encircling band having an inside surface adapted to contact the neck of a wearer of the collar and an outside surface;

a chin support brace having a first end and a second end and a concave edge separated by said first end and said second end; and hinge means connecting said elongated neck encircling band to said chin support brace for rotating said chin support brace from an inoperable position being substantially parallel to said elongated neck encircling band and adjacent to the inside surface of the elongated neck encircling band to an operable position being more than 180 degrees from the inoperable position relative to the elongated neck encircling band.

BRIEF DESCRIPTION OF THE DRAWINGS

FIG. 5 illustrates a cross section of a hinge of the collapsible cervical collar in a flattened configuration.

FIG. 6 illustrates a cross section of the hinge mechanism of the collapsible cervical collar of FIG. 5 in an operable configuration.

DETAILED DESCRIPTION OF THE INVENTION

The collapsible cervical collar has an elongated neck encircling band and a chin support brace. The chin support brace has first and second ends and a concave edge separating the first and second ends. A hinge means connects the elongated neck encircling band to the chin support brace. The hinge means enables the chin support brace to rotate more than 180 degrees from an inoperable position, that is coplanar with the elongated neck encircling band, to an operable position. The collapsible cervical collar is collapsible from an operable configuration to a flattened configuration.

The hinge means is, desirably, a first hinge and a second hinge. One of these two hinges is located at each of the first and second ends of the chin support brace. The first hinge and the second hinge are separated from one another by a concave edge of the chin support brace. The first hinge and the second hinge define an intermediate section or curve of the chin support brace. The first hinge and the second hinge can each be a grooved strip of material or similar structure.

An alternative embodiment of the hinge means can also be a pin hinge recessed within the elongated neck encircling band. An attaching means affixes each pin hinge to the elongated neck encircling band. The attaching means can be a rivet, nut and bolt, pin and lock, or other suitable attaching mechanisms.

A connecting means connects a first end of the elongated neck encircling band to a second end of the elongated neck encircling band. The connecting means can include hook and loop fabric such as that sold under the trade name Velcro™, a nut and bolt affixed through aligned apertures, or similar structures.

A padding means is attached to an interior surface of the elongated neck encircling band and an interior surface of the chin support brace. The padding means can be any cushioning material, such as conventional foam pads.

Figure 1:
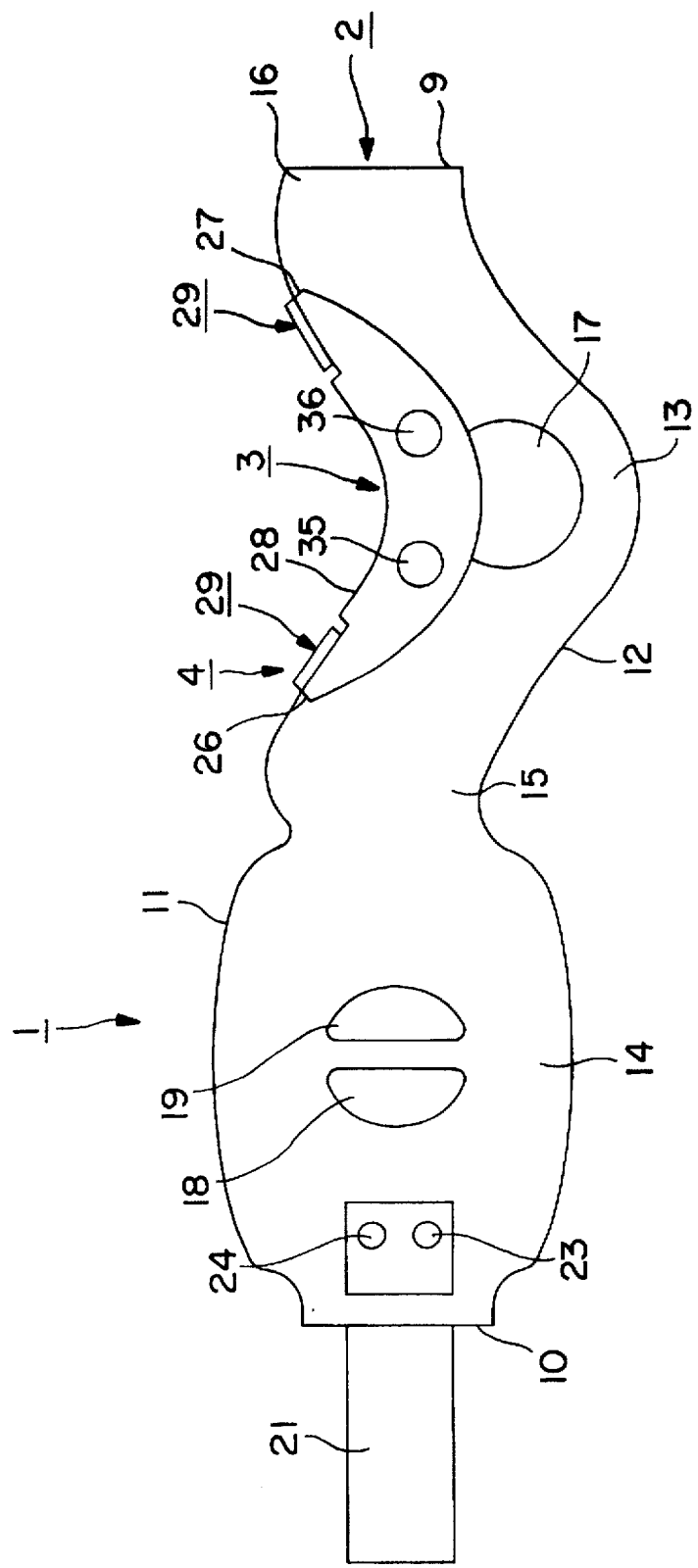
FIG. 1 illustrates the collapsible cervical collar in a flattened configuration as viewed from the surface adjacent to a wearer of the device.

FIG. 1 illustrates a collapsible cervical collar in a flattened configuration as viewed from the surface adjacent to a wearer of the device. The collapsible cervical collar 1 has an elongated neck encircling band 2 connected to an elongated crescent-shaped chin support brace 3 by a hinge 29.

The elongated neck encircling band 2 is asymmetrical. The elongated neck encircling band 2 has a first end 9, a second end 10, an upper edge 11, a lower edge 12, an operable front 13, an operable back 14, an operable left side 15, and an opposing operable right side 16. The cervical collar 1 is placed on a user or patient such that the interior of the operable front 13 of the elongated neck encircling band 2 is placed against the front portion of the neck under the chin. The operable back 14 of the elongated neck encircling band 2 is placed against the back of the user's neck. The operable front 13 of the elongated neck encircling band 2, desirably, has an aperture 17 to provide tracheal and/or carotid access. The operable back 14 of the elongated neck encircling band 2 has one or more apertures 18 and 19 to provide ventilation to the back of the neck.

The crescent-shaped chin support brace 3 has a hinge assembly 4. The chin support brace 3 has a first end 26 separated from a second end 27 by a concave edge 28 and, desirably, has cut-out portions 35 and 36 to reduce the weight of the collapsible cervical collar 1. The concave edge 28 is connected to the upper edge 11 of the elongated neck encircling band 2 by a hinge 29. A fastening strap 21 is affixed to the elongated neck encircling band 2 with snap fittings 23 and 24.

Figure 2:
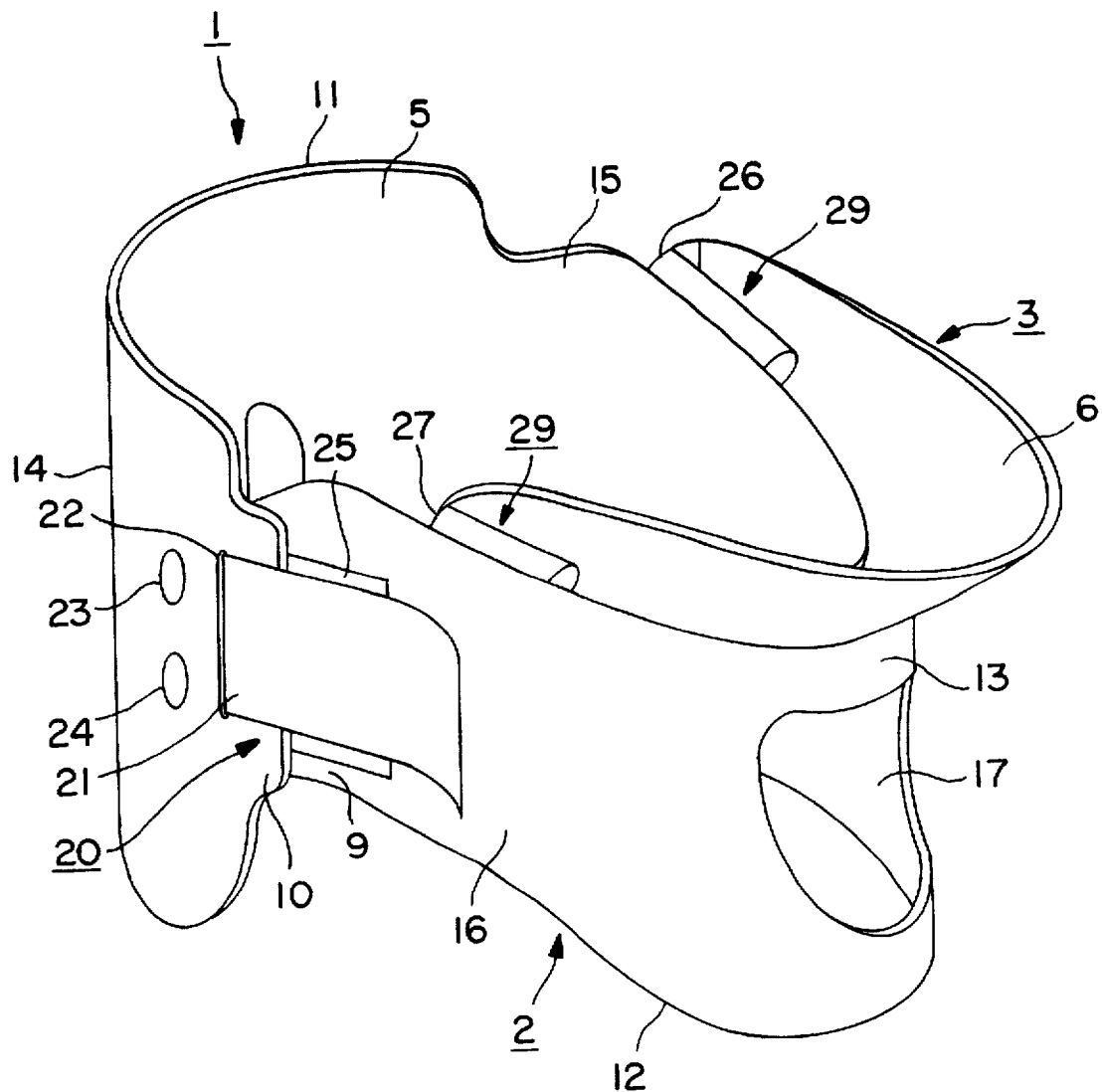
FIG. 2 illustrates the collapsible cervical collar of FIG. 1 in an operable configuration.

FIG. 2 illustrates the collapsible cervical collar of FIG. 1 in an operable configuration. A linking mechanism 20 secures the first end 9 and the second end 10 of the elongated neck encircling band 2 together to form the elongated neck encircling band into a substantially tubular, operable configuration.

Figure 3:
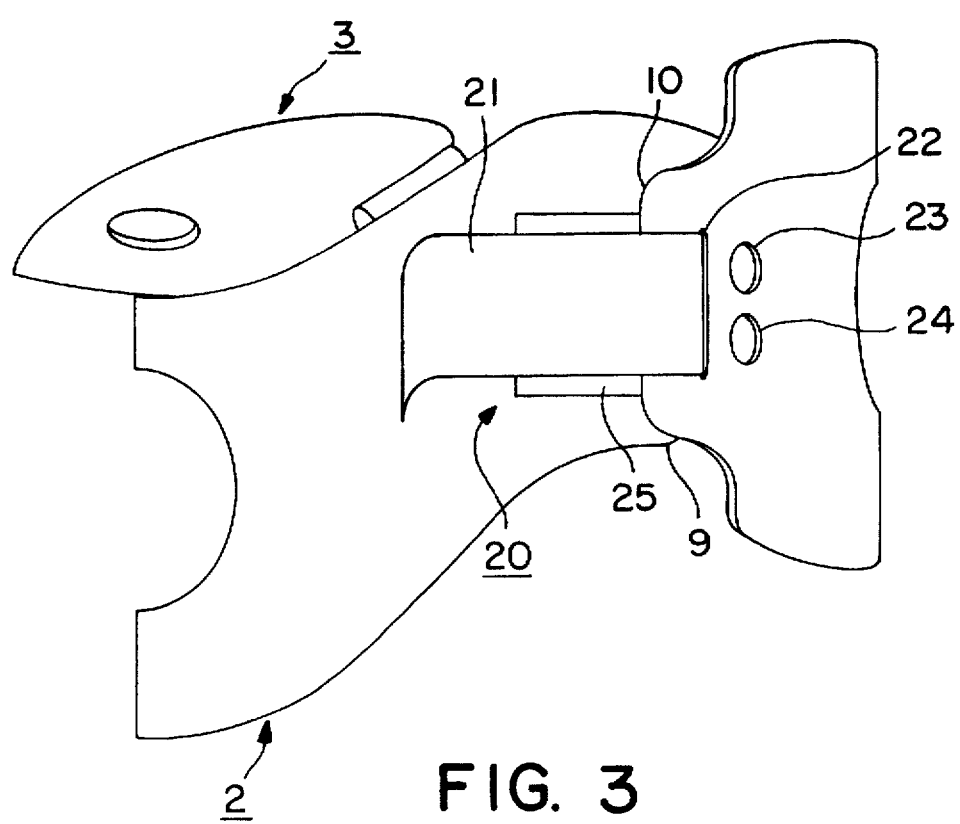
FIG. 3 illustrates a side view of the collapsible cervical collar of FIG. 1 in the operable configuration.

FIG. 3 illustrates side view of the collapsible cervical collar of FIG. 1 in the operable configuration. A linking or affixing mechanism 20 can be provided by any conventional strap or fastening means that can hold the first end 9 and the second end 10 of the elongated neck encircling band 2 together. For example, a strip of loop fabric 21 is passed through an elongated slot 22 and secured to the interior of the second end 10 of the elongated neck encircling band 2 by bolts or rivets 23 and 24. A corresponding strip of hook fabric 25 is secured to the exterior surface of the first end 9 of the elongated neck encircling band 2 by conventional securing methods, such as adhesives. Upon contact, the loop fabric 21 and hook fabric 25 secure the first end 9 and the second end 10 of the elongated neck encircling band 2 together to form the elongated neck encircling band 2 into the operable configuration.

Figure 4:
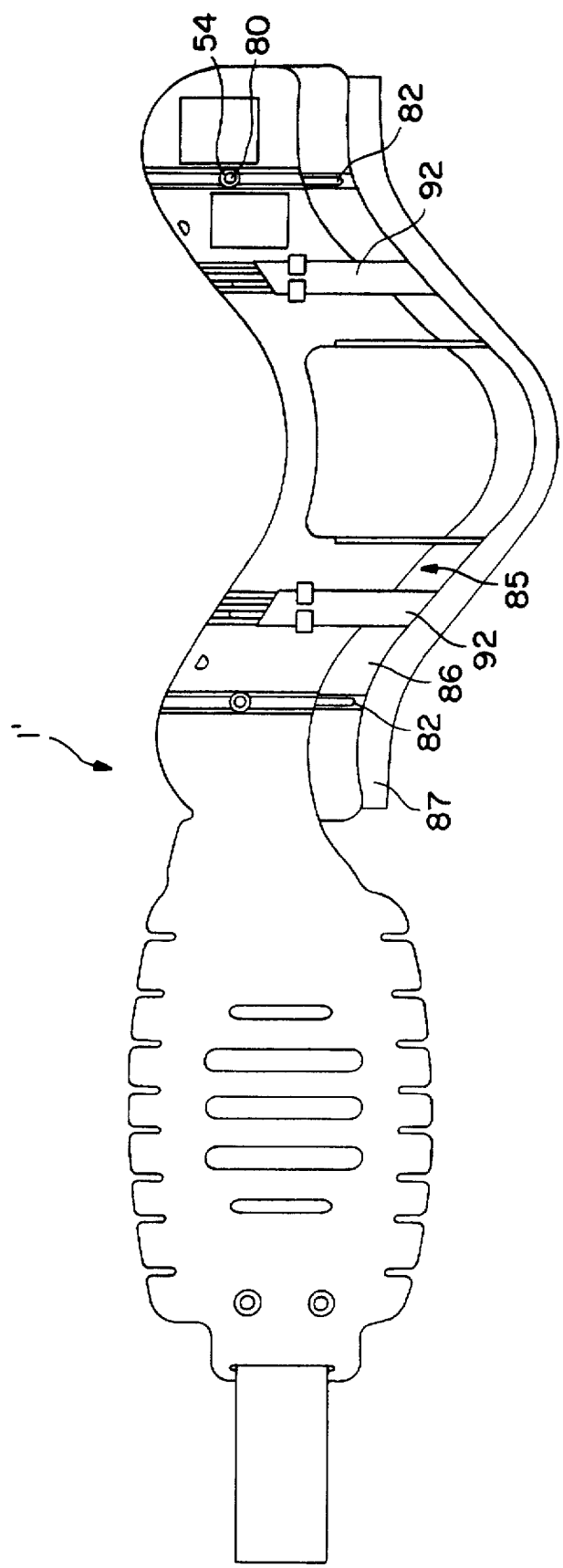
FIG. 4 illustrates an automatic adjustable neck band for use with the collapsible chin support of this invention.

FIG. 4 illustrates an automatic adjustable neck band 1' for use with the collapsible chin support of this invention. A neck encircling band 85 is adjustably affixed to a shoulder brace 86. The neck encircling band 85 receives a post 80 that passes through slot 82 of the shoulder brace 86. The post 80 is secured with a fastener 54. The shoulder brace is adjusted in height relative to the neck encircling band 85 by a pawl and ratchet slide 92. The surface of the automatic adjustable neck band 1' worn next to a patient has a foam pad 87.

FIG. 5 illustrates a cross section of a hinge of the collapsible cervical collar of FIG. 1 in the flattened configuration. For comfort, a soft, cushioning material 7 and 8 can be secured to the interior surface 5 of the elongated neck encircling band 2 and to the interior surface 6 of the chin support brace 3. The cushioning material 7 and 8 can include conventional foam pads.

The pads can be secured to the interior surface 5 of the elongated neck encircling band 2 and to the interior surface 6 of the chin support brace 3 by any conventional securing means such as adhesives or snap fasteners. It is preferred that the cushioning material 7 and 8 be secured by cement or similar adhesive to reduce the number of parts of the cervical collar 1.

FIG. 6 illustrates a cross section of the hinge of the collapsible cervical collar of FIG. 5 in the operable configuration. The elongated neck encircling band 2, chin support brace 3, and hinge 29 are formed as a single, integral member of synthetic resin. This structure is, desirably, formed by injection molding of a plastic. The hinge 29 has hinging grooves 30 and 31 at the first end 26 of the chin support brace 3 and hinging grooves 32 and 33 at the second end 27 of the chin support brace 3. A first pair of hinging grooves 31 and 32 is positioned along the concave edge of the chin support brace 3. A second pair of hinging grooves 30 and 33 is spaced from the first pair of hinging grooves 31 and 32. An intermediate rigid section 34 is formed between the first hinging grooves 31 and 32 and the second hinging grooves 30 and 33.

The cervical collar 1 can be collapsed into a flattened configuration by separating the loop fabric 21 and hook fabric 25 of the elongated neck encircling band affixing mechanism 20. The chin support brace 3 is rotated inwardly toward the interior surface 5 of the elongated neck encircling band 2.

The hinging grooves 30, 31, 32, and 33 enable the chin support brace 3 to rotate to a flattened configuration. The direction of elongation of the chin support brace 3 is parallel to the direction of elongation of the elongated neck encircling band 2 in the flat position. In this relationship, the chin support brace 3 and elongated neck encircling band 2 are coplanar. The intermediate section 34 connects, and is perpendicular to, the elongated neck encircling band 2 and the chin support brace 3. The intermediate section 34 provides space for the cushioning material 7 and 8. The cervical collar 1 is formed into a flattened configuration with the interior surface 6 of the chin support brace 3 adjacent the interior surface 5 of the elongated neck encircling band 2, as shown in FIGS. 1 and 5. The interior patient contacting surfaces 5 and 6 are positioned on one side of the flattened elongated neck encircling band 2. Multiple cervical collars 1 can thus be stored hygienically in a minimum amount of space.

Once flattened, the cervical collar 1 is converted easily to an operational configuration. Connecting the hook fabric 21 and loop fabric 25 forms the elongated neck encircling band 2 into the operable configuration. The chin support brace 3 is rotated outwardly to project across the upper edge 11 of the elongated neck encircling band 2, as shown in FIGS. 2 and 6. The chin support brace 3 and the intermediate section 34 effect a single unified member and form an angle of approximately 90 degrees and 180 degrees with the elongated neck encircling band 2. A stopping means or extension 40 adjacent to the second pair of hinging grooves 30 and 33 supports the chin support brace 2 and intermediate section 34 in the operable configuration.

The axes of the first pair of hinging grooves 31 and 32 and the axes of the second pair of hinging grooves 30 and 33 are oblique with respect to one another. Each pair of axes intersects at a point (not shown) that bisects the neck encircling band 2. The oblique relationship of the axes of the hinging grooves 30, 31, 32, and 33 causes the chin support brace 3 to bend outwardly from the operable front 13 and opposing left and right sides 15 and 16 of the neck encircling band 2. The bow of the chin support brace 3 and elongated neck encircling band 2 support the head against lateral flexion and axial rotation.

Figure 7:
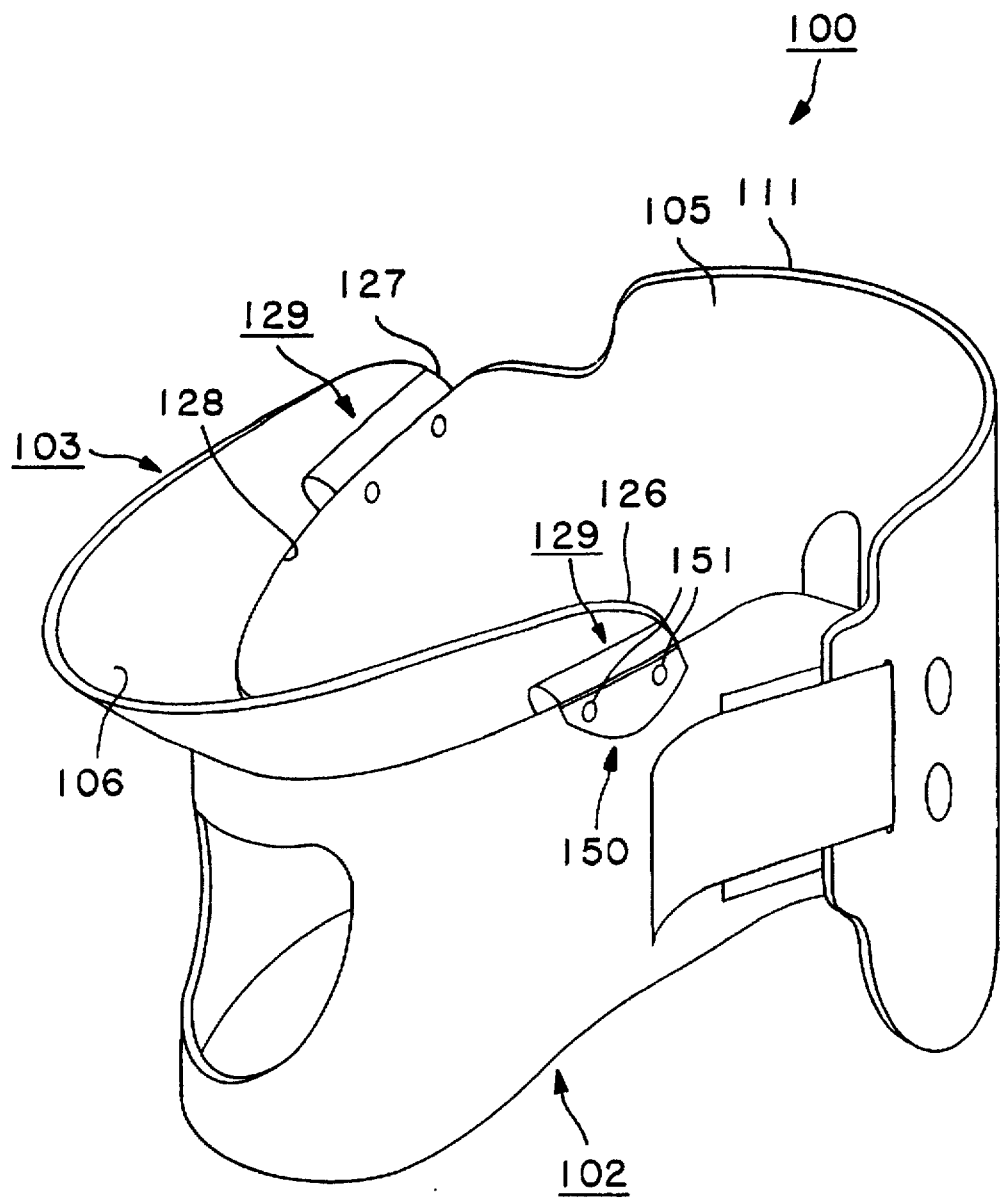
FIG. 7 illustrates a collapsible cervical collar in an operable configuration in accordance with an alternative embodiment of the invention.

FIG. 7 illustrates a collapsible cervical collar in an operable configuration in accordance with an alternative embodiment of the invention. The chin support brace 103, elongated neck encircling band 102, and hinge 129 are formed as separate components in this embodiment of the collapsible cervical collar 100.

Figure 8:
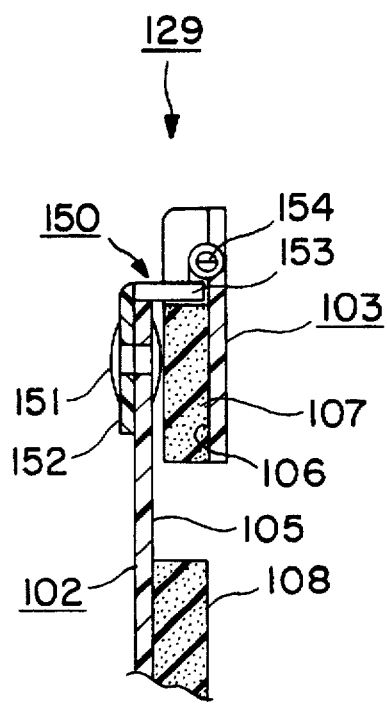
FIG. 8 illustrates a cross section of a hinge mechanism of the collapsible cervical collar of FIG. 7 in a flattened configuration.

FIG. 8 illustrates a cross section of a hinge of the collapsible cervical collar of FIG. 7 in a flattened configuration. An L-shaped bracket 150 is attached to the outside of the elongated neck encircling band 102 by a bolt or rivet 151 at locations adjacent each end of the chin support brace 103. A first section 152 of each L-shaped bracket 150 extends along the outside surface of, and parallel to, the elongated neck encircling band 102. A second section 153 of each L-shaped bracket 150 extends perpendicular to the first section 152. Each second section 153 extends across and overhangs the upper edge 111 of the elongated neck encircling band 102.

Figure 9:
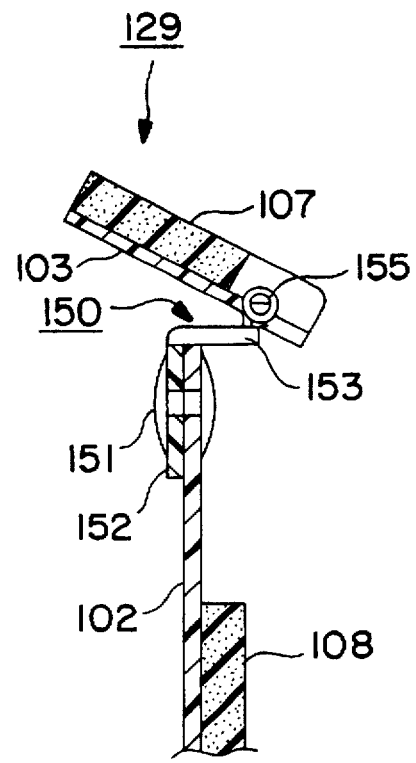
FIG. 9 illustrates a cross section of the hinge mechanism of the collapsible cervical collar of FIG. 7 in an operable configuration.

FIG. 9 illustrates a cross section of the hinge mechanism of the collapsible cervical collar of FIG. 7 in the operable configuration. A pair of hinges 154 and 155 are recessed into the chin support brace 103 at the concave edge 128. Each hinge 154 and 155 is connected to the overhanging end of the second section 153 of the corresponding L-shaped bracket 150. The hinges 154 and 155 enable the chin support brace 103 to be rotated to a flattened configuration where the direction of elongation of the chin support brace 103 is parallel to the direction of elongation of the elongated neck encircling band 102. The L-shaped brackets 150 provide space for the cushioning material 107 and 108. The cervical collar 100 forms into a flattened configuration with the interior surface 106 of the chin support brace 103 adjacent the interior surface 105 of the elongated neck encircling band 102, as shown in FIG. 8. The cervical collar 100 is converted to an operable configuration shown as in FIG. 9 in a manner similar to that of the embodiment of FIG. 2.

Figure 10:
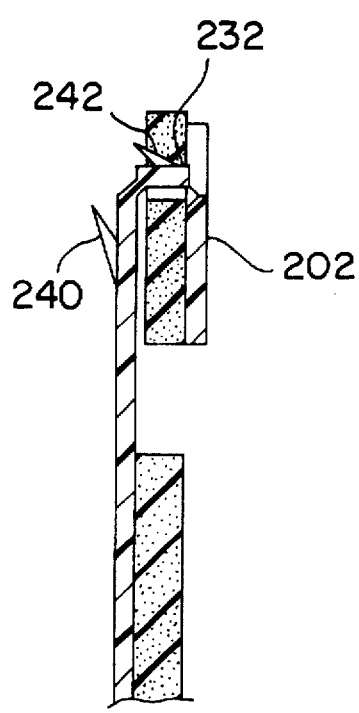
FIG. 10 illustrates a cross section of a hinge mechanism in accordance with another embodiment of a collapsible cervical collar in a flattened configuration.

FIG. 10 illustrates a cross section of a hinge in accordance with another embodiment of an collapsible cervical collar in a flattened configuration. This alternative embodiment replaces the stopping means or extension 40 that supports the chin support brace 3 and intermediate section 34 in the operable configuration of the embodiment of FIGS. 5 and 6 with a pair of communicating extensions 240 and 242.

Figure 11:
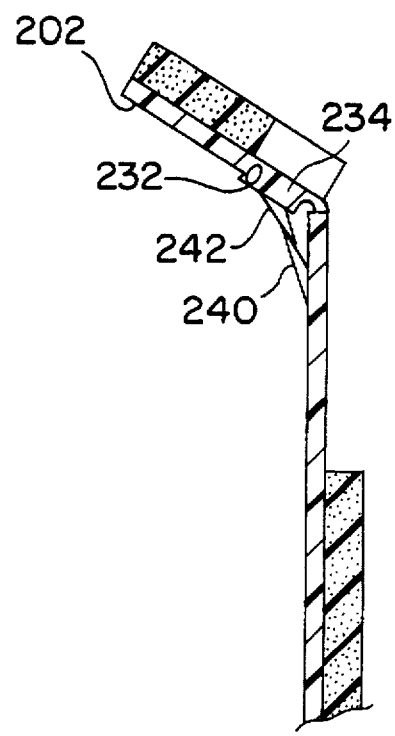
FIG. 11 illustrates a cross section of the hinge mechanism in accordance with the embodiment of the collapsible cervical collar of FIG. 10 in an operable configuration.

FIG. 11 illustrates a cross section of the hinge in accordance with the embodiment FIG. 10 of the collapsible cervical collar in an operable configuration. The pair of communicating extensions 240 and 242 support the chin support brace 202 and intermediate section 234 in the operable configuration.

Figure 12:
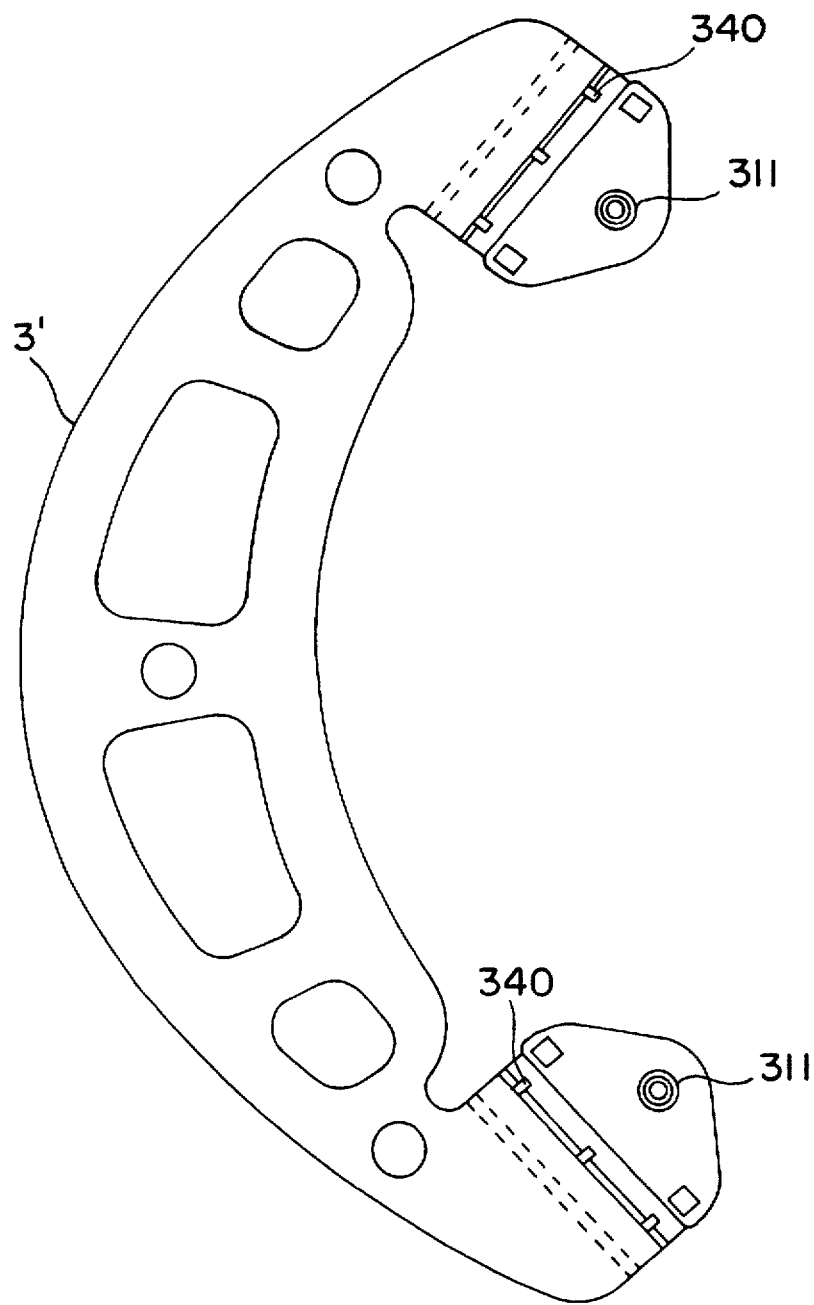
FIG. 12 illustrates a chin support brace of the collapsible cervical collar of the preferred embodiment of the invention.

FIG. 12 illustrates a chin support brace 3' of the collapsible cervical collar of the preferred embodiment of the invention. This chin support brace 3' is affixed to a neck encircling band with rivets (not shown) placed through holes 311. This chin support brace 3' can, alternatively, be injection molded as a single piece with a neck encircling band.

Figure 13:
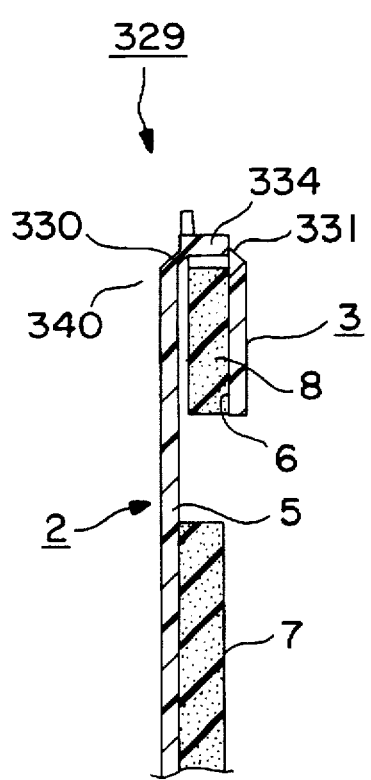
FIG. 13 illustrates a cross section of a hinge mechanism, in accordance with embodiment of a collapsible cervical collar of FIG. 12, in a flattened configuration.

FIG. 13 illustrates a cross section of a hinge 329, in accordance with embodiment of a chin support brace 3' of FIG. 12, in a flattened configuration. The chin support brace 3' and the intermediate section 334 effect a single unified member and form an operable angle of approximately 90 degrees with the elongated neck encircling band 2. A stopping means or extension 340 adjacent to the second pair of hinging grooves 330 and 333 supports the chin support brace 3' and intermediate section 334 in the operable configuration.

The axes of the first pair of hinging grooves 331 and 332 and the axes of the second pair of hinging grooves 330 and 333 are oblique with respect to one another. Each pair of axes intersects at a point (not shown) that bisects the neck encircling band 2. The oblique relationship of the axes of the hinging grooves 330, 331, 332, and 333 causes the chin support brace 3' to bend outwardly from the operable front 13 and opposing left and right sides 15 and 16 of the neck encircling band 2. The bow of the chin support brace 3 and elongated neck encircling band 2 support the head against lateral flexion and axial rotation.

Figure 14:
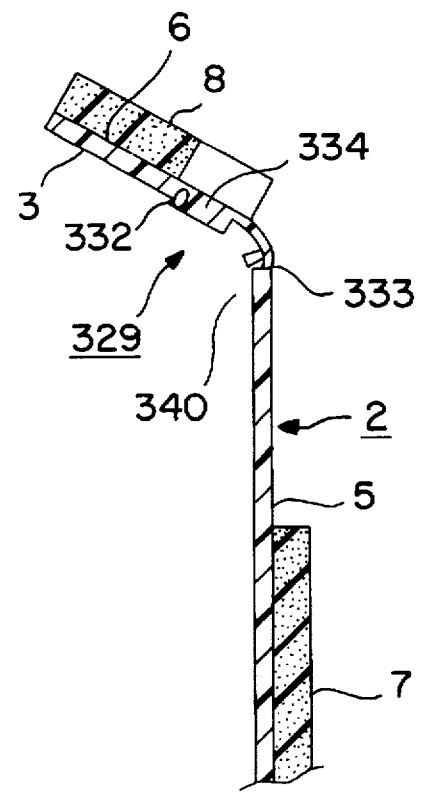
FIG. 14 illustrates a cross section of the hinge mechanism, in accordance with the embodiment of the collapsible cervical collar of FIG. 12, in an operable configuration.

FIG. 14 illustrates a cross section of the hinge mechanism, in accordance with the embodiment of the chin support brace 3' of FIG. 12, in an operable configuration.

The collapsible cervical collar of the invention is formed from a stiff, sturdy, and light-weight synthetic resin, such as high density polyethylene or polyvinyl chloride. The elements of the cervical collar can be die cut, extruded, or prepared from molds as is conventional in the industry. However, in the preferred embodiment, the elongated neck encircling band, chin support brace, and hinge are injection molded in one piece from synthetic resin. Manufacturing the cervical collar in this manner is simple, fast, and inexpensive.

The collapsible cervical collar is stored in a flattened configuration with the interior surface of the elongated neck encircling band adjacent the interior surface of the chin support brace. The collapsible cervical collar is place into an operable condition by turning or rotating the chin support brace more than 180 degrees relative to the elongated neck encircling band in order to project outwardly from the operable front of the neck encircling band. The cervical collar is placed on a patient with the interior of the front portion of the elongated neck encircling band placed against the front portion of the neck under the chin of the patient. The front portion of the elongated neck encircling band is held in place while the remainder of the elongated neck encircling band is bent to conform to the neck of the patient. The strip of loop fabric is brought into contact with the strip of hook fabric to secure the cervical collar in position. If the adjustable neck encircling band is used with the chin support brace of this invention, the shoulder brace is adjusted to the height of the patient by the pawl and ratchet slide and locked.

The collapsible cervical collar is collapsible into a substantially flattened configuration and reduces the storage space required for the device. The collar is collapsible when fully assembled and does not require assembly prior to use.

The hinges of the chin support brace are durable and reliable. The hinges are not significantly weakened through successive use.

I claim:

1. A collapsible cervical collar comprising:

an elongated neck encircling band having an inside surface adapted to contact the neck of a wearer of the collar and an outside surface;

a chin support brace having a first end and a second end and a concave edge separated by said first end and said second end; and hinge means connecting said elongated neck encircling band to said chin support brace for rotating said chin support brace from an inoperable position being substantially parallel to said elongated neck encircling band and adjacent to the inside surface of the elongated neck encircling band to an operable position being more than 180 degrees from the inoperable position relative to the elongated neck encircling band.

2. The collapsible cervical collar according to claim 1, wherein said hinge means is at least one hinge at said first end and at least one hinge at said second end of the chin support brace.

3. The collapsible cervical collar according to claim 2, wherein said at least one hinge at said first end and said at least one hinge at said second end are pin hinges, said pin hinges are recessed within said chin support brace.

4. The collapsible cervical collar according to claim 3, further comprising attaching means for attaching each pin hinge to said elongated neck encircling band.

5. The collapsible cervical collar according to claim 2, wherein the elongated neck encircling band and the chin support brace are a single integral member of injection molded resin.

6. The collapsible cervical collar according to claim 1, wherein said hinge means includes a stopping means.

7. The collapsible cervical collar according to claim 6, wherein said stopping means supports said chin support brace in said operable position on said neck encircling band.

8. The collapsible cervical collar according to claim 7, wherein the neck encircling band has an aperture to expose a larynx.

9. The collapsible cervical collar according to claim 1, wherein said hinge means include at least one grooved portion.

* * * * *

UNITED STATES PATENT AND TRADEMARK OFFICE
CERTIFICATE OF CORRECTION

PATENT NO. :   5,797,863
DATED      :   August 25, 1998
INVENTOR(S):   KØHNKE, Ole It is certified that error appears in the above-identified patent and that said Letters Patent is corrected as shown below:

Column 2, line 35, delete "separated by" and substitute therefor --separating--.

Column 7, line 22, delete "place" and substitute therefor --placed--.

Column 8, line 8, delete "separated by" and substitute therefor --separating--.

Signed and Sealed this

Fifteenth Day of December, 1998

Attest:

BRUCE LEHMAN

Attesting Officer

Commissioner of Patents and Trademarks